Figure 1:
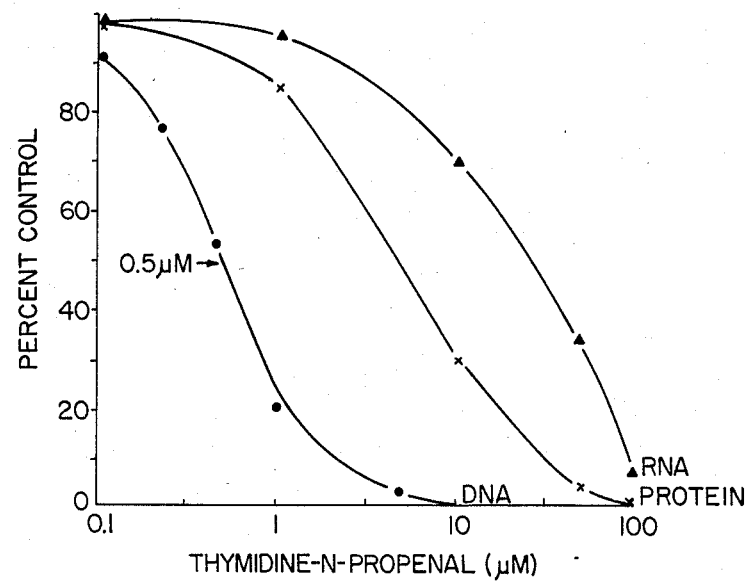
Figure 2:
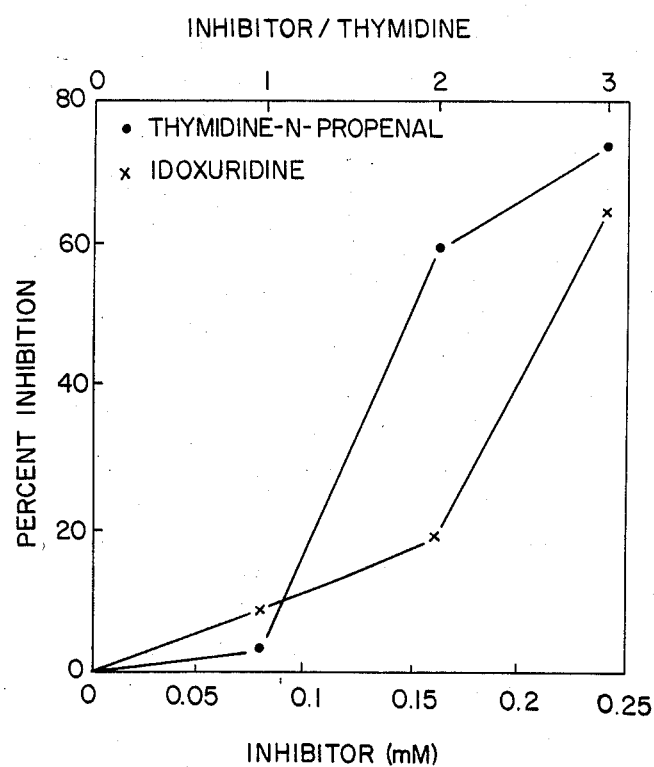

United States Patent [19]

Johnson et al.

[11] Patent Number: 4,689,321
[45] Date of Patent: Aug. 25, 1987

[54] OXO PROPENYL NUCLEOSIDES AND NUCLEOSIDE RELATED ANALOGS

[75] Inventors: Francis Johnson, Setauket; Arthur P. Grollman, E. Setauket, both of N.Y.

[73] Assignee: The Research Foundation of State University of New York, Albany, N.Y.

[21] Appl. No.: 633,108

[22] Filed: Jul. 20, 1984

[51] Int. Cl.⁴ .................. A61K 31/70; C07H 17/00
[52] U.S. Cl. ............................. 514/45; 514/46; 514/49; 514/50; 536/23; 536/24; 536/26
[58] Field of Search ............... 536/23, 24, 26; 514/49, 514/50, 45, 46

[56] References Cited

U.S. PATENT DOCUMENTS 3,376,283  4/1968  Hunter ................................. 536/23
4,171,431  10/1979  Skulnick .............................. 536/29
4,267,171  5/1981  Bergstrom et al. ................. 514/49

FOREIGN PATENT DOCUMENTS 0095292  11/1983  European Pat. Off. ............. 536/23
0018697  1/1982  Japan ................................. 536/23

Primary Examiner—Johnnie R. Brown
Assistant Examiner—John W. Rollins, Jr.

[57] ABSTRACT

Certain 3-oxo-prop-1-enyl purine and pyrimidine derivatives and the corresponding nucleosides have been prepared. These compounds exhibit interesting and valuable cytotoxic activity. This cytotoxicity is of special interest in that it appears to inhibit DNA reproduction without affecting RNA or protein synthesis.

15 Claims, 2 Drawing Figures

OXO PROPENYL NUCLEOSIDES AND NUCLEOSIDE RELATED ANALOGS

The work described in the present application has been supported in part by Grant No. CA1739501 from the Dept. of Health and Human Sciences, Public Health Service.

BACKGROUND OF THE INVENTION

One of the principal problems encountered in the search for novel and effective antineoplastic compounds is to provide compounds which are cytotoxic with respect to the neoplastic cells but which do not negatively affect other essential physiological functions of the system in which they are administered. It is desired, therefore, to provide compounds which will inhibit DNA replication but will not, at inhibitory concentrations, affect RNA or protein synthesis.

SUMMARY OF THE INVENTION

It has been found that the presence of the 3-oxo-prop-2-enyl moiety on certain bases provides compounds which are cytotoxic to neoplastic cells without adversely affecting RNA and protein synthesis.

The compounds of the present invention are β-amino-α,β-unsaturated carbonyl compounds of the following general structural formula:

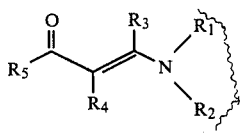
(I)

wherein

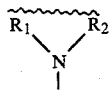

is a substituted or unsubstituted monocyclic or fused bicyclic heterocyclic moiety containing 1, 2 or 3 nitrogen atoms in each ring, said rings containing 5, 6 or 7 ring atoms; $R_3$ and $R_4$ are hydrogen or lower alkyl, $R_5$ is hydrogen, lower alkyl, or an ester residue of the formula —$COR_6$ wherein $R_6$ is alkyl, aralkyl, or aryl.

The lower alkyl groups referred to herein preferably contain 1-6 carbon atoms and include methyl, ethyl, propyl, butyl, pentyl, hexyl and the corresponding branched chain isomers thereof.

The term "aryl" as used herein refers to phenyl and phenyl substituted by one or more substituent groups selected from among chloro, bromo, fluoro, lower alkyl, hydroxy, nitro, amino, aminomethyl, halolower alkyl, lower monoalkylamino, lower dialkylamino, lower alkoxy and carboxy. Such aryl groups can be, for example, 4-hydroxyphenyl, 3,4-dichlorophenyl, 2,6-dimethoxyphenyl, 4-methylphenyl, 2-fluorophenyl, 4-carboxyphenyl, 3-nitrophenyl, 4-aminophenyl, 3-aminophenyl, 4-dimethylaminophenyl, 4-aminomethylphenyl and 4-ethoxyphenyl.

The term "aralkyl" encompasses aryl-substituted lower alkyl groups such as benzyl, phenethyl, p-fluorobenzyl, o-tolylethyl and m-hydroxyphenethyl.

The term "halo" refers to fluoro, chloro, bromo and iodo substituents.

The lower alkoxy groups referred to herein likewise contain 1-6 carbon atoms and are exemplified by methoxy, ethoxy, propoxy, and the like.

More specifically, the present invention includes compounds having the pyrimidyl nucleus as well as the 2-aza analogs thereof having the following general formulae:

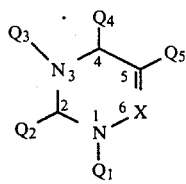 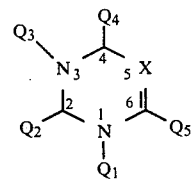

IIa  IIb wherein $Q_1$ is hydrogen, a pentosyl moiety, or the group

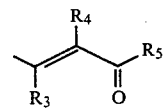

wherein $R_3$, $R_4$ and $R_5$ are as defined in Formula I; $Q_3$ is hydrogen or the group

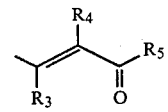

wherein $R_3$, $R_4$ and $R_5$ are as defined in Formula I; $Q_2$ and $Q_4$ are hydrogen oxo or imino (i.e., =NH); $Q_5$ is hydrogen, halo, trihalomethyl, lower alkoxyalkyl, lower alkyl or 2(E)- or 2(Z) -bromovinyl; X is methylene or aza; with the proviso that $Q_1$ and $Q_3$ are not the same. Where $Q_4$ is H and $Q_1$ is other than H there must be a double bond between atoms 3 and 4 of the ring. Similarly, when $Q_2$ is H and $Q_3$ is other than H there must be a double bond between atoms 1 and 2 of the ring. Thus, in formulae IIa and IIb, $Q_2$ and $Q_4$ may not simultaneously be hydrogen.

Suitably, the compounds of Formula IIa have a uracilyl, cytosinyl, thyminyl, 4-oxopyrimidyl, or 4-aminopyrimidyl nucleus. The oxopropenyl substituent can be attached thereto at the 1 or 3 positions, i.e., $Q_1$ or $Q_3$. Also within the scope of the invention are the corresponding nuclei having a pentosyl substituent at the 1-position, especially those with a 2'-deoxyuridinyl, 2'-deoxycytidinyl or 2'-deoxythymidinyl nucleus. Suitably, the pentose may be ribose, arabinose, or 2'-deoxyribose. The ring substituents at the 2 and 4-positions are suitably oxo or imino (or its enamine tautomeric form). A plurality of substituents is permitted on the oxopropenyl moiety provided that the basic structure is maintained. Included among these substituents are hydrogen, lower alkyl and the ester residue of the formula —$COR_6$ wherein $R_6$ is alkyl, aralkyl, or aryl.

The purine analogs and their 8-aza analogs of the foregoing pyrimidine derivatives of Formula II are also included within the scope of the present invention and have the following general formula III:

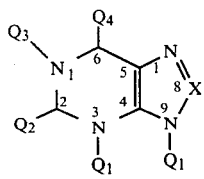

(III)

wherein $Q_1$, $Q_2$, $Q_3$ and $Q_4$, are as defined in Formula II; $Q_1'$ is identical to $Q_1$, except that when $Q_1$ is pentosyl it will generally be found at the 9-position. Suitably, the compounds of Formula III have a guaninyl, adeninyl, xanthinyl or hypoxanthinyl nucleus. Also within the scope of the invention are the corresponding nuclei having a pentosyl substituent at the 9-position, especially those having a guanosinyl, adenosinyl, xanthosinyl or inosinyl nucleus. Suitably, the pentose may be ribose, arabinose or 2'-deoxyribose. In the case of the pentosyl substituted compounds, the oxypropenyl moiety will be at the 1 or 3-position rather than at the 9-position. The ring substituents at the 2- and 6-positions are suitably oxo or amino. A plurality of substituents is permitted on the oxypropenyl moiety provided that the basic structure is maintained. Included among these substituents are hydrogen, lower alkyl and the ester residue of the formula —$COR_6$ wherein $R_6$ is alkyl, aralkyl or aryl.

Several methods of synthesis are available for the compounds of the present invention. The particular method utilized will depend upon the particular starting material. Generally, a solution of the appropriate monocyclic or bicyclic heterocyclic moiety is added to propargyl aldehyde (substituted or unsubstituted), at low temperatures, typically from about −70° C. to about 0° C. in the presence of an acid acceptor. The solvent system is a nonhydroxylic polar solvent such as dimethylformamide, acetone, acetonitrile or mixtures thereof. The acid acceptor utilized may be an organic or inorganic base, such as a tertiary amine such as triethylamine or sodium ethoxide. Dimethylformamide in the presence of a substantially equal molar amount of a base such as triethylamine at dry ice temperatures is especially suitable for the conduct of this type of reaction in the case of nucleosides. Similarly, the reaction may commence at slightly higher temperatures, say up to about −25° C.

Where the desired oxopropenyl moiety has non-hydrogen $R_3$, $R_4$ and $R_5$ substituents, a carbonyl starting material having the desired substituents already in place must be employed. Where for example, the entering group is of the type —CH=C(R)CHO, —C(R)=CH-CHO or —CH=CHCOR, a suitable starting material would be one having a chloro moiety attached to the terminal carbon carrying the double bond. Preparation of such compounds is well known in the art.

In certain situations, it will be necessary to block the oxo groups of the moncyclic or bicyclic heterocyclic moiety prior to the addition of the aldehyde. This is accomplished according to standard procedures well known in the chemical arts, see for instance, Zorbach and Tipsen, "Nucleic Acid Chemistry", Volume 1, page 388. Typical blocking agents include trimethylsilyl and dimethyl-t-butylsilyl. When the aldehyde has been added, the blocking groups can be readily removed by the addition of water or a trace of acid.

It will be understood by those skilled in the art that a problem of nomenclature exists where trivial names are not used. The problem arises from the existance of keto and enol forms of oxygen ring substitution. Thus, the terms pyrimidyl and purinyl will be used for compounds of general Formula II and III irrespective of the nature of substituents $Q_2$ and $Q_4$.

The cytotoxic activity of the compounds of the present invention is determined by screening methods standard for the determination of such activity.

The results for the testing of the effect of a representative compound of the present invention, 3-(thymidin-3-yl)-prop-2-enal) in a murine leukemia model, are given in Table I wherein the foregoing compound is designated as XX-336.

TABLE I

| Material | Treatment Schedule | Dose, IP mg/kg/inj | MST Days | Effect MST % T/C | AWC gm d.5 | Survivors d.5 (30) |
|---|---|---|---|---|---|---|
| XX-336 | d.1 | 256 | TOX | TOX | TOX | 0/4 |
|  |  | 128 | TOX | TOX | TOX | 0/4 |
|  |  | 64 | TOX | TOX | TOX | 0/4 |
|  |  | 32 | 8.0 | 123 | +0.5 | 3/4 |
|  |  | 16 | 8.5 | 131 | +0.5 | 4/4 |
|  |  | 8 | 10.0 | 154 | +2.1 | 4/4 |
|  | qd 1 5 | 64 | TOX | TOX | TOX | 1/4 |
|  |  | 32 | TOX | TOX | TOX | 1/4 |
|  |  | 16 | 9.5 | 146 | +0.8 | 4/4 |
|  |  | 8 | 9.5 | 146 | +0.4 | 4/4 |
|  |  | 4 | 8.0 | 123 | +0.6 | 4/4 |
|  |  | 2 | 8.0 | 123 | −0.3 | 4/4 |
| Control |  | Saline | 6.5 | — | +2.7 | 10/10 |

Tumor Inoculum: $10^6$ ascites cells implanted i.p.
Host: $CFD_{1+}$° mice
Tox: <4/6 or <3/4 mice aline on d.5
Evaluation: MST = median survival time
Effect: % T/C = (MST treated/MST control) × 100.
Criteria: % T/C > 125 considered significant antitumor activity.

Additional test results of 3-(thymidin-3-yl)-prop-2-enal, against tumor cell growth another compound of the present invention, are given in Table II below.

TABLE II

Effects of 3-(thymidin-3-yl)-prop-2-enal on Tumor Cell Growth in Culture

| Cell Line | $IC_{50}$ $\mu M$ |
|---|---|
| L-1210 Leukemia[a] | 1.6 |
| Lewis lung carcinoma[a] | 5.9 |
| B-16 melanoma[a] | 4.2 |
| DLD-1 human colon carcinoma[b] | 5.0 |

[a]Testing performed at Roswell Park Memorial Institute. See proposal for methodology and references.
[b]Testing performed at Brown University. Cell lines and methodology described in Am. J. Med., 71, 949 (1981).

Inhibitor effects of 3-(thymidin-3-yl)-prop-2-enal are given in Table III below.

TABLE III

Effects of Inhibitors on Synthesis of DNA and TTP in HeLa Cells

| Compound | Conc. $\mu M$ | Inhibition DNA Synthesis[a] % | TTP Formation[b] % |
|---|---|---|---|
| 3-(Thymidin-3-yl)-prop-2-enal | 0.1 | 6 | 6 |
|  | 0.3 | 38 | 50 |
|  | 1.0 | 70 | 75 |
|  | 2.0 | 88 | 85 |
|  | 20.0 | 100 | 95 |

[a]Measured, over a period of 60 min., as described in the Legend to FIG. II.
[b]HeLa cells were suspended for 30 min. in 2 ml. of minimal essential media containing 25 uCi of $^3H$—thymidine. Cells were lysed, carrier nucleotides added and $^3H$—TTP isolated by thin layer chromatography.

Additionally, Fig. I indicates that the cytotoxicity of 3-(3-oxoprop-1-enyl)-2'-deoxythymidine is associated dominantly with the inhibition of DNA synthesis.

As cytotoxic agents, the compounds of this invention have utility in the treatment of numerous disease states involving the proliferation of cells, i.e., treatment of solid cancerous tumors, lung, colon and rectal cancers, blood disorders such as leukemia, skin diseases such as psoriasis, mycosis, fungoides and vitiligo.

The compositions of the present invention comprise a compound of Formula I in a cytotoxic amount together with a suitable pharmaceutical carrier. A cytotoxic amount is defined as the amount of compound necessary to inhibit DNA reproduction without affecting RNA or protein synthesis. In the usual course of therapy, the active compound is incorporated into an acceptable vehicle to form a composition for oral, intramuscular, intravenous or topical administration.

Compositions for oral administration may be exemplified by tablets, capsules, pills, lozenges, dragees, powders, granulates, solutions, suspensions or elixirs.

Typical intramuscular or intravenous formulations are injectable solutions and suspensions.

Compositions for topical application may be ointments, creams, lotions, solutions, suspensions, aerosols, gels, shampoos, soaps or dusting powders.

Typical acceptable pharmaceutical carriers for use in the formulations described above are exemplified by: sugars such as lactose, sucrose, mannitol and sorbitol; starches such as corn starch, tapioca starch and potato starch; cellulose, ethyl cellulose and methyl cellulose; calcium phosphates such as dicalcium phosphate and tricalcium phosphate; sodium sulfate; calcium sulfate, polyvinylpyrrolidine; polyvinyl alcohol; stearic acid; alkaline earth metal stearates such as magnesium stearate and calcium stearate; stearic acid vegatable oils such as peanut oil, cottonseed oil, sesame oil, olive oil and corn oil; nonionic, cationic and anionic surfactants; ethylene glycol polymers, B-cyclodextrin; fatty alcohols; and hydrolyzed cereal solids. Other ingredients to the compositions of the present invention may be preservatives, coloring, flavoring, sweetening, thickening, suspending, dispersing, emulsifying, swelling, stabilizing, and buffering agents as required by the specific formulation.

The required daily dosage may be administered in single or divided doses. The exact dose to be administered will, of course, be dependent upon various factors such as the particular compound employed, the particular disease state involved, the route of administration, the age and weight of the patient and his or her individual response to the treatment regimen.

The following Examples describe in detail compounds, compositions and methods illustrative of the present invention. It will be apparent to those skilled in the art that many modifications, both of materials and methods, may be practical without departing from the purpose and intent of this disclosure.

EXAMPLE I 3-(Thyminyl-1-yl)-prop-2-enal

A mixture of thymine (504 mg, 4 mmol) and BSTFA (7 ml) is heated at 120° protected from moisture for 2 hours. At the end of this time all the thymine goes into solution indicating complete silylation of thymine. This is cooled to room temperature and propargyl aldehyde (432 mg, 8 mmol) is added in one lot and the mixture stirred for 1 hour. Water is added very slowly to the reaction mixture. The precipitate obtained was washed with cyclohexane until the cyclohexane layer showed no color. The desired product is isolated and crystallized from methanol as white powder (580 mg; 76.5%) M.P. 215°–218° C. The NMR spectrum of the material is in agreement with the postulated structure and shows absorption peaks at (DMSO) 1.84 (3H, d, J = 1 Hz,CH$_3$) 6.47 (q,J = 7.8 Hz J2 = 14.8 Hz, 1H, —CH=CH—C$\overline{H}$O) 8.04 (S,1H,4$\underline{H}$) 8.17 (d, J = 7.5 Hz, —C$\underline{H}$=C$\overline{H}$—CHO) 9.58 (d, J = 7.5 Hz, 1H, —CH=CH—C$\overline{H}$O). Mass spectrum M/Z (intensity, % of base peak), ion:180 (12), M$^+$, 152 (100) (M-CO)$^+$ 151 (35) (M-HCO)$^+$, 126 (20) (M-C$_3$H$_3$O)$^+$ 109 (40) 80 (50).

EXAMPLE II 3-(Adenin-9-yl) prop-2-enal

To a suspension of adenine (135 mg; 1 mmole) in dimethylformamide (2 ml) at −40° there is added a solution of sodium ethoxide (prepared from 15 mg of sodium hydride) in ethanol (1 ml) and the mixture is stirred for 10 min. Propargyl aldehyde (59 mg; 1.1 mmole) is added in one portion and stirring is continued at −40° for 1 hr. The pale brown reaction mixture is then allowed to come to room temperature and neutralized by the addition of aqueous ammonium chloride. The precipitated solid (100 mg) is removed by filtration. It is recrystallized by dissolution in boiling water (240 ml) followed by cooling. This affords to the pure title compound (100 mg., 52.9%) m.p. 258°–60° C. The NMR spectrum of the material is in agreement with the postulated structure and shows absorption peaks at (DMSO) 7.17 (q,J$_1$ = 7.8 HzJ$_2$ = 14.4 Hz, 1H, —CH=CH—CHO) 7.55 (S, 2H, NH$_2$) 8.28 (S, 1H) 8.54 (d, J, J = 14.4 Hz, 1H C$\underline{H}$=CH—CHO) 8.64 (S, 1H) 9.68 (d, J-7.9 Hz, CHO). Mass spectrum m/z (intensity, % of base peak), ion: 189 (55.7)M$^+$, 161 (98) (M-CO)$^+$, 160 (32) (M-HCO)$^+$, 134 (100) (MC$_3$H∂)M$^+$, 161 (98) (M-CO)$^+$, 160 (32) (M-HCO)$^+$, 134 (100) (MC$_3$H$_3$O)$^+$, 118 (93).

EXAMPLE III 3-(Thymidin-3'-yl) prop-2-enal

Thymidine (488 mg, 2 mmol) is dissolved in dimethylformamide (4 ml), triethylamine (280 μl; 2 mmole) is added and the mixture is stirred for 1 hr. then cooled to −78°. Propargyl aldehyde (200 μl; 4 mmole) is added and the mixture is stirred at this temperature for 2 hrs. and then allowed to come to room temperature over a period of 3 hrs. The solvent and triethylamine are removed under reduced pressure at room temperature. The residue is dissolved in methanol and applied to two preparative tlc plates (20×20 cm; silica gel, 2 mm thick). The plates are developed with ethyl acetate containing 5% methanol. The desired product has R$_f$0.65 and is detected by means of a thiobarbituric acid coloration test (pink). The starting material has an R$_f$ of 0.4. Removal of the appropriate band from the plates, followed by extraction with methanol affords the title compound as an almost colorless glass (220 mg, 35%) which crystallized on standing m.p. 121°–2°. The infrared spectrum shows bands at 3425 (OH), 1733 (CHO), 1690, 1660, 1295, 1260, 1150, 1095, 1040 cm$^{-1}$. The NMR spectrum has absorption bands at (DMSO) 1.85 (S, 3H, CH$_3$) 6.19 (t, J = 6.1 Hz, 1H, O—CH—N) 7.06 (q,J, = 7.8 Hz J$_2$ = 14.8 Hz 1H, CH=CH—C$\overline{H}$O) 7.95 (s, 1H, 4$\underline{H}$) 8.16 (d, J = 14.6 Hz, 1H, C$\underline{H}$=CH—CHO) 9.60

(d, J=7.8 Hz, 1H, C$\underline{H}$O) in addition to the peaks usually observed for thymidine the NH at 11.28 excepted. Mass spectrum m/z (intensity % of base peak), ion: 296 (0.4)M+, 242(2.0) (M-54)+, 180 (4.0) (M-117)+, 117 (100) (M-180)+, 73 (71)C$_3$H$_3$O.

EXAMPLE IV

3-(5'-Iodo-2'-deoxyuridin-3'-yl)prop-2-enal

5-Iodo-2'-deoxyuridine (142 mg; 0.4 mmole) in dimethylformamide (2 ml) is treated with triethylamine (56 μl, 0.4 mmole) and the mixture is stirred at room temperature for 1 hr. then cooled to −70° C. Propargyl aldehyde (40 μl; 0.8 mmole) is added in one portion, stirring is continued for 1 hr. and the solution is allowed to warm slowly to 10° C. The solvent and triethylamine are removed at room temperature under reduced pressure and the residue is chromatographed on two 20×20 cm preparative TLC plates (silica gel). The eluting solvent used is ethyl acetate and the band running just head of starting material gives a positive thiobarbituric acid test. This is removed and the silica gel extracted with methanol. Removal of the solvent affords the title compound as an almost colorless glassy solid (40 mg; 25% yield) by pure TLC analysis. $^1$HNMR (DMSO) 6.09 (t, J=6.1 Hz, 1H, —C$\underline{H}$(O) N). 7.04 (q,J=7.8 Hz, J$_2$=14.8 Hz, 1H CH=CHC$\underline{H}$O) 8.5 (d,J=14.8 Hz, 1H, —CH=CH—CHO) 8.59 (s, 1H, N—C$\underline{H}$)=C(I) 9.60 (d,J=7.7 Hz, 1H, CH=CH—C$\underline{H}$O). Mass spectrum m/z (intensity, % base peak), ion: 408 (0.1)+, 379 (9.1) (M-CHO)+ 354 (0.1) (M—CH=CH—CHO)+ 317 (27.8), 263 (53) 195 (31.5) 117 (100).

EXAMPLE V

3-(2'-Deoxyuridin-3'-yl)prop-2-enal

The procedure used in Example IV is followed utilizing 2'-deoxyuridine (456 mg; 2 mmole) triethylamine (280 μl; 2 mmole) and propargyl aldehyde (200 μl; 4 mmole) to obtain, after preparative TLC (eluant 5% methanol in ethyl acetate), the desired title compound as a pale yellow oil (190 mg; 34% yield) pure by TLC analysis. $^1$HNMR (DMSO) 5.88 (d, J=8.2 Hz, 1H, N—CH=CH—CO) 6.15 (t,J=6.1 Hz, 1H, N—C$\underline{H}$—(O)), 7.04 (q, J$_1$=8.2 Hz, J$_2$=14.8 Hz, 1H, —CH=CH—CHO) 8.05 (d,J=8.2 Hz, 1H, N—CH=CH—CO) 8.15 (d,J=14.8, 1H, C$\underline{H}$=CH—CHO) 9.60 (d,J=7.8 Hz, 1H, C$\underline{H}$O). Mass spectrum m/z (intensity, % base peak), ion: 282 (0.1)M+, 253 (0-1) (M-CHO)+, 137 (40) 117 (78) 73 (100).

EXAMPLE VI

3-(Uridin-3'-yl)prop-2-enal

The procedure used for the preparation of the compound of Example V is followed utilizing uridine (508 mg, 2 mmole), triethylamine (280 μl, 2 mmole) and propargyl aldehyde (200 μl, 4 mmol). The title compound is obtained after preparative TLC (eluent 10% methanolethylacetate, Rf 0.4) as a colorless oil (160 mg, 31%) pure by TLC analysis. $^1$HNMR (DMSO) 5.79 (d,J=3.5 Hz, 1H, O—C$\underline{H}$—N) 5.88 (d, J=8.4 Hz, 1H, COC$\underline{H}$=CH—) 7.05 (q, J$_1$=7.7 Hz, J$_2$14.8 Hz, 1H —C$\underline{H}$=CH—CHO) 8.14 (d, J=8.2 Hz, 1H, N—CH=CH—) 8.16 (d,J=14.7 Hz, 1H —CH=CH—C$\underline{H}$O), 9.60 (d, J=7.7 Hz,1H, C$\underline{H}$O). Mass spectrum m/z (intensity, % of base peak) 298 (0.1)M+, 270 (2) (M-CO)+244 (40) (M-C$_3$H$_3$O)+.

EXAMPLE VII

3-(Thymidin-3'-yl) acrylonitrile

The title compound is obtained by following essentially the same method described in Example V. Thus starting from thymidine (360 mg, 1.5 mmol), triethylamine (210 μl, 1.5 mmol) and acetylene cyanide. (152 mg, 3 mmol), the title compound is obtained after purification on preparative TLC (5% methanol in ethyl acetate, Rf 0.45), as a slight yellow oil (140 mg, 35%) pure by TLC analysis. $^1$HNMR, (DMSO) 1.86 (s, 1H,-CH$_3$) 6.17 (t,J=6.1 Hz, 1H, —O—C$\underline{H}$—N) 6.18 (d, J=9 Hz, 1H, —CH=CH—CN) 7.06 (d,J=9 Hz, 1H, —CH=CH—CN) 7.89 (s,1H, N—C$\underline{H}$=C—CH$_3$).

EXAMPLE VIII

1-(thymidin-3'-yl)but-1-en-2-one

The compound is obtained by the method described in Example V starting from thymidine (242 mg; 1 mmol), triethylamine (140 μl, 1 mmol) and butyn-2-one (136 mg, 2 mmol) as an oil (30 mg, 12%) pure by TLC analysis. (5% methanol, ethylacate, Rf 0.55) $^1$HNMR (DMSO) as an oil (30 mg, 12%) pure by TLC analysis. (5% methanol, ethylacate, Rf 0.55) $^1$HNMR (DMSO) 1.85 (s,3H,CH$_3$) 2.27 (s,3H,COCH$_3$) 6.17 (t, J=6.1 Hz, —N—C$\underline{H}$—O—) 7.19 (d, J=15 Hz, 1H —CH=CH—COCH$_3$) 7.91 (s,1H, —N—C$\underline{H}$=C—CH$_3$) 8.02 (d, J=15 Hz,1H, CH$_3$COC$\underline{H}$=CH—N).

EXAMPLE IX

3-(Cytosin-1'-yl)prop-2-enal

Cytosine (330 mg) is silylated by heating at 110° C. with BSTFA (3 ml) for 2 hrs. The silylated product is suspended in anhydrous acetonitrile (5 ml) at room temperature and propargyl aldehyde (300 mg) is added to it. The mixture is stirred for 4 hrs. and the solid separated is filtered, washed with ethyl acetate, dried and crystallized from water to afford the title product as white needles, 80 mg, mp 255°-57° C. (decomp). TLC analysis, shows only a single spot Rf (0.4, 3:1 ethyl acetate, methanol), $^1$HNMR (DMSO 5.92 (d, J=7.7 Hz, H$_6$) 6.38 (q,J$_1$=7.6 Hz, J$_2$=14.7 Hz, —CH=CH—CHO) 7.87 (s,2H, NH$_2$) 8.04 (d, J=7.7 Hz, H$_5$) 8.26 (d,J=14.7 Hz —CH=CH—CHO) 9.55 (d, J=7.6 Hz, 1H, CHO), MS. m/z (intensity 1% of base peak) 165 (2.2)M+, 137 (17.7) M-28, 136 (100) M-29.

EXAMPLE X

1-phenyl-3-(thymin-1'-yl)prop-2-enone

To a solution of thymine (126 mg) in dimethylformamide (3 ml) is added triethylamine (130 μl). The mixture is stirred for 1 hr. To this is added, dropwise, a solution of phenylethynyl ketone (156 mg) in dimethylformamide (3 ml), over a period of five minutes and the mixture is allowed to stand overnight. It is then neutralized with acetic acid, and the dimethylformamde is removed in vacuo at room temperature. The product is washed three times with hot methanol (5 ml each time) and recrystallized in dimethylformamide/methanol. The title compound is a white solid with m.p. 257°-59° C. (decomposed). TLC analysis shows a single spot (rf=0.75, ethyl acetate). $^1$HNMR (300 MHz, in DMSO-d$_6$), 1.89 (d, J=0.9 Hz, 3H, —CH$_3$), 7.51 (d, J=14.1 Hz, 1H,H-1'), 7.58 (t, J=7.5 Hz, 2H,H-3"and −5"), 7.67 (dd, J$_1$=7.2 Hz, J$_2$=1.2 Hz, 1H, H-4"), 8.11 (dd, J$_1$=7.8 Hz, J$_2$=1.2 Hz,2H, H-2" and −6"), 8.23 (d, J=14.1 Hz, 1H, H-2'), 8.40 (q, J=0.9 Hz, 1H, H-6), Ms, m/z (relative intensity) 256 (5.0) M+, 151 (100) M+-C7H5O, 105 (29.7) M+-C7H7N2O2.

EXAMPLE XI 1-(4'-Methoxyphenyl)-3-(thymin-1'-yl)prop-2-enone

To a solution of thymine (126 mg) in dimethylformamide (3 ml) is added triethylamine (130 μl). The mixture is then stirred for 1 hr. To this is added, dropwise, a solution of p-methoxyphenyl ethynyl ketone (190 mg) in dimethylformamide (3 ml) over a period of five minutes. After 6 hrs., the reactl ethynyl ketone (190 mg) in dimethylformamide (3 ml) over a period of five minutes. After 6 hrs., the reaction mixture is neutralized with acetic acid, and the dimethylformamide is removed in vacuo at room temperature. The product is washed three times with hot methanol (5 ml each time), and recrystallized in dimethylformamide/methanol. The title compound is a white solid with m.p. 246°-48° C. (decomposed). TLC analysis shows a single spot (Rf=0.7, ethyl acetate). $^1$H NMR (DMSO-$d_6$), 1.9 (bs, 3H, —CH3), 3.67 (s, 3H, —OCH3), 7.07 (d, J=8.9 Hz, 2H, H-3" and —5"), 7.46 (d, J=14.0 Hz, 1H, H-2'), 8.26 (bs, 1H, H-6), Ms, m/z (relative intensity) 286 (10) M+, 151 (100) M+-C8H8O2, 135 (36) M+-C7H7N2O2.

EXAMPLE XII 3-(5'-Fluorouracil-l-yl)prop-2-cnal

Fluorouracil (130 mg) is dissolved in dimethylformamide (3 ml) and a catalytic amount (20 mg) of sodium ethoxide in 0.5 ml ethanol is added. The mixture is stirred for 1 hr., cooled to −50° C., and propargyl aldehyde (100 ul) is added. The mixture is allowed to come slowly to room temperature and stirred for 4 hrs. This solution is then neutralized with acetic acid and the precipitate filtered, washed with ethyl acetate and dried to afford the title compound as a white solid, 70 mg, mp. 235°-38° (decomp). TLC analysis shows only single spot—(Rf=0.6, ethyl acetate) $^1$H NMR (DMSO , 6.38 (q,$J_1$=7.5 Hz, $J_2$=14.5 Hz, —CH=CH—CHO), 8.11 (dd, $J_1$=2 Hz, $J_2$=14.5 Hz,1H, —C$\overline{H}$=CH—CHO) 8.36 (d, J=7.5 Hz,1H, H6) 9.58 (d, J=$\overline{7.5}$ Hz,1J, CHO), Ms. m/z (intensity 1% of base peak) 184 (1) M+, 156 (100) M-28, 155 (30) M-29, 113 (45) M-71.

EXAMPLE XIII

2-Methyl-3-(thymin-1'-yl)but-2-enal

To a solution of thymine (126 mg; 1 mmole) in dimethylformamide (4 ml) is added sodium ethoxide (72.5 mg, 1.1 mmole), and 3-chloro-2-methyl-2-butenal (118 mg; 1 mmole). The mixture then is allowed to stand at 60° C. overnight. It is neutralized by acetic acid, and the dimethylformamide is removed in vacuo at room temperature. The resulting product is purified by column chromatography. The title compound is obtained as a white solid (m.p. 223°-226° C. decomposed) which shows only a single spot (Rf, 0.5; ethyl acetate) on TLC analysis. $^1$H NMR (CDCl3), 1.89 (m, 3H, —C(CH3))=C(CH3)CHO) 1.94 (d, J=1.1 Hz, 3H, —CH3) 2.23 (m, 3H, =C(CH3)CHO) 6.96 (d,J=1.1.94 (d, J=1.1 Hz, 3H, -CH3) 2.23 (m, 3H, =C (CH3)CHO) 6.96 (d, J=1.1 Hz, 1H, 9.69 (S, 1H, —CHO) MS, m/z, (intensity %C (CH3)CHO) 6.96 (d, J=1.$\overline{1}$ Hz, 1H, 9.69 (S, 1H, —CHO) MS, m/z, (intensity % base peak), 2.08.2, (1.2) $\overline{M}$+, 180.2 (12.4) M-28, 179.2 (100) M-29.

EXAMPLE XIV

Utilizing the procedures described in Examples I-XIII with the appropriate starting materials, namely (5-bromo-2'-deoxyuridine) and propargyl aldehyde;
(5-fluoro-2'-deoxyuridine) and propargyl aldehyde;
3 -phenylpropargyl aldehyde and cytosine;
3-phenylpropargyl aldehyde and 5-methylcytosine;
3-phenylpropargyl aldehyde and 5-methoxymethylcytosine
propargyl aldehyde and 5-methylcytosine;
propargyl aldehyde and 5-methoxymethylcytosine;
propargyl aldehyde and 5-(2(E)-bromovinyl)cytosine;
propargyl aldehyde and 5-trifluoromethylcytosine;
propargyl aldehyde and 5-trifluoracil;
propargyl aldehyde and 5-ethyluracil;
propargyl aldehyde and 5-ethoxyethyluracil;
3-phenylpropargyl aldehyde and thymine;
propargyl aldehyde and 4-oxopyrimidine;
propargyl aldehyde and 4-aminopyrimidine;
uridine and propargyl aldehyde;
3'-acetylpropargyl aldehyde and cytosine;
3'-benzoylpropargyl aldehyde and thymine;
quanine and propargyl aldehyde;
xanthine and propargyl aldehyde;
xanthine and propargyl aldehyde;
xanthine and propargyl aldehyde;
hypoxanthine and propargyl aldehyde;
8-azaguanine and propargyl aldchyde;
3-phenylpropargyl aldehyde and guanine;
3-phenylpropargyl aldehyde and xanthine;
3-phenylpropargyl aldehyde and hypoxanthine;
3-m-fluorophenylpropargyl aldehyde and 8-azaguanine;
propargyl aldehyde and guanosine;
3-phenylpropargyl aldehyde and guanosine;
propargyl aldehyde and inosine;
propargyl aldehyde and xanthosine;
propargyl aldehyde and xanthosine;
propargyl aldehyde and quanosine;
propargyl aldehyde and inosine;
propargyl aldehyde and xanthosine;
propargyl aldehyde and deoxyguanosine; and
1-arabinoxylthymine and propargyl aldehyde
the following compounds of this invention are obtained:
3-(5-bromo-2'-deoxyuridin-3-yl) prop-2-enal;
3-(5-fluoro-2'-deoxyuridin-3-yl) prop-2-enal;
1-(1-phenylprop-1'-ene-3'-al )cytosine;
1-(1-phenylprop-1'-ene-3'-al )-5-methylcytosine;
1-(1-phenylprop-1'-ene-3'-al )-5-methoxymethyl-cytosine;
1-(1-prop-1-en-3-a1)-5-methylcytosine;
1-(1-prop-1-en-3-al)-5-methoxymethylcytosine;
1-(1-prop-1-en-3-al)-5-(2(E)-bromovinyl)cytosine;
1-(1-prop-1-en-3-al)-5-trifluoromethylcytosine;
1-(1-prop-1-en-3-al)-5-trifluorouracil;
1-(1-prop-1-en-3-al)-5-ethyluracil;
1-(1-prop-1-en-3-al)-5-ethoxyethyluracil;
3-(3-phenylprop-1'-ene-3'-one)thymine;
1-(1-prop-1-en-3-al)-4-oxopyrimidine;
1-(1-prop-1-en-3-al)-4-aminopyrimidine;
3-(uridin-3-yl) prop-2-enal;
1-(3'-acetylprop-1'-ene-3'-al)cytosine;
1-(3'-benzoylprop-1'-ene-3'-al )thymine;
3-(quaninyl-3-yl) prop-2-enal;
3-(xanthinyl-9-yl) prop-2-enal;
3-(xanthinyl-3-yl) prop-2-enal;
3-(xanthinyl-9-yl) prop-2-enal;
3-(hypoxanthinyl-9-yl) prop-2-enal;

3-(8-azaguaninyl-9-y1)-prop-2-enal;
9-(1'-phenylprop-1'-ene-3'-al )guanine;
9-(1'-phenylprop-1'-ene-3'-al )xanthine;
9-(1'-phenylprop-1'-ene-3'-al )hypoxanthine;
9-(1'-m-fluorophenylprop-1'-ene-3'-al )-8-azaguanine;
9-(1-prop-1-en-3-al)-8-azaguanine;
1-(1-prop-1-en-3-al)guanosine;
1-(1'-phenylprop-1'-ene-3'-al)guanosine;
1-(1-prop-1-en-3-al) inosine;
3-(1-prop-1-en-3-al) xanthosine;
1-(1-prop-1-en-3-al) xanthosine;
3-(1-prop-1-en-3-al)guanosine;
3-(1-prop-1-en-3-al) inosine;
3-(1-prop-1-en-3-al)xanthosine;
1-(1-prop-1-en-3-al)deoxyguanosine;
3-(1-arabinoxylthymin-3-yl)prop-2-enal;

We claim:

1. An imino propenylcarbonyl compound of the structure:

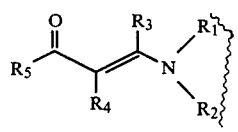

wherein

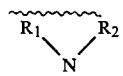

is a substituted or unsubstituted monocyclic or fused bicyclic heterocyclic moiety containing 2 or 3 nitrogen atoms in each ring, said rings containing 5, 6, or 7 ring atoms, $R_3$ and $R_4$ are hydrogen or lower alkyl, $R_5$ is hydrogen, lower alkyl, or an ester residue of the formula $—COR_6$ wherein $R_6$ is alkyl, aralkyl, or aryl.

2. A compound of claim 1 wherein a pentosyl moiety is bonded to one of the ring nitrogen atoms.

3. A compound of claim 2 wherein the pentose is selected from the group consisting of ribose, arabinose, and 2-deoxyribose.

4. A compound of claim 2 wherein the heterocyclic moiety is selected from the group consisting of uridinyl, cytidinyl and thymidinyl.

5. A compound of claim 2 wherein the heterocyclic moiety is selected from the group consisting of guanosinyl, adenosinyl, xanthosinyl and inosinyl.

6. A compound of claim 2 which is 3-(thymidin-3'-yl) prop-2-enal.

7. A compound of claim 2 wherein the heterocyclic moiety is selected from the group consisting of purinyl, azapurinyl and pyrimidyl.

8. A compound of claim 2 wherein the six membered ring system is substituted by 0, 1, or 2 members of the group consisting of =O and $—NH_2$.

9. A compound of claim 2 wherein the heterocyclic moiety is selected from the group consisting of uracilyl, cytosinyl, thyminyl, 4-oxopyrimidyl and 4-aminopyrimidyl.

10. A compound of claim 2 wherein the heterocyclic moiety is selected from the group consisting of guaninyl or adeninyl, xanthinyl or hypoxanthinyl.

11. A compound of claim 2 which is 3-(thymin-1'-yl) prop-2-enal.

12. A compound of claim 2 of the formula

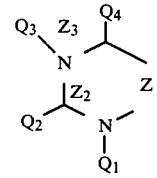

wherein $—Z—$ is

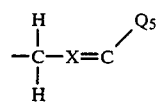

$Z_3$ and $Z_2$ are carbon carbon double or carbon carbon single bonds
wherein $Q_1$, H, pentosyl or
wherein $R_3$, $R_4$ and $R_5$ are as in claim 3
$Q_3$ is H or

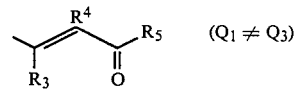

wherein $R_3$, $R_4$ and $R_5$ are as in claim 3
$Q_4$ is H, oxo or imino,
$Q_5$ is H, halo trifluoromethyl, lower alkoxyalkyl or 2(E) or 2(Z) bromovinyl,
X is methylene or aza
provided that $Q_1$ and $Q_3$ are different
and where $Q_4$ is H and $Q_1$ is other than H, $Z_3$ is a carbon carbon double bond
and where $Q_2$ is H and $Q$ is other than H, $Z_2$ is a carbon carbon double bond.

13. A pharmaceutical composition comprising a cytotoxic amount of a compound of claim 1 together with a pharmaceutical carrier compatible with cal composition comprising a cytotoxic amount of a compound of claim 1 together with a pharmaceutical carrier compatible with said compound.

14. A composition according to claim 13 wherein the compound is 3-(thymin-1'-yl)prop-2-enal.

15. A composition according to claim 13 wherein the compound is 3-(thymidin-3-yl) prop-2-enal. -enal.